(12) United States Patent
Barve et al.

(10) Patent No.: US 6,504,050 B1
(45) Date of Patent: Jan. 7, 2003

(54) PROCESS FOR THE PREPARATION OF 2-ACRYLAMIDO-2-METHYL-1-PROPANESULFONIC ACID

(75) Inventors: Prashant Purushottam Barve, Maharashtra (IN); Sunil Shankar Joshi, Maharashtra (IN); Ravindra William Shinde, Maharashtra (IN); Milind Yashwant Gupte, Maharashtra (IN); Chandrashekhar Narayan Joshi, Maharashtra (IN); Shrikant Madhukar Ghike, Maharashtra (IN); Raghavendra Venkatrao Naik, Maharashtra (IN); Rajendra Anantrao Kulkarni, Maharashtra (IN); Aruna Narayan Bote, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/096,070

(22) Filed: Mar. 13, 2002

(51) Int. Cl.$^7$ .............................................. C07C 309/00
(52) U.S. Cl. ...................................................... 562/105
(58) Field of Search ........................................... 562/105

(56) References Cited

U.S. PATENT DOCUMENTS

| | | | | |
|---|---|---|---|---|
| 3,506,707 A | * | 4/1970 | Miller | |
| 3,544,597 A | * | 12/1970 | Killam | |
| 3,547,899 A | * | 12/1970 | Arlt | |
| 6,448,347 B1 | * | 9/2002 | Quinn | |

* cited by examiner

Primary Examiner—Michael L. Shippen
(74) Attorney, Agent, or Firm—Nixon & Vanderhye P.C.

(57) ABSTRACT

The present invention provides a process for the preparation of highly pure 2-acrylamido-2-methyl-1-propanesulfonic acid in high yield, with improved appearance, by the reaction of acrylonitrile with more than 98% sulfuric acid or oleum and liquefied isobutylene in presence of weak inorganic acids or organic sulfonic acids.

12 Claims, 1 Drawing Sheet

PROCESS FOR THE PREPARATION OF 2-ACRYLAMIDO-2-METHYL-1-PROPANESULFONIC ACID

FIELD OF THE INVENTION

Figure 1:
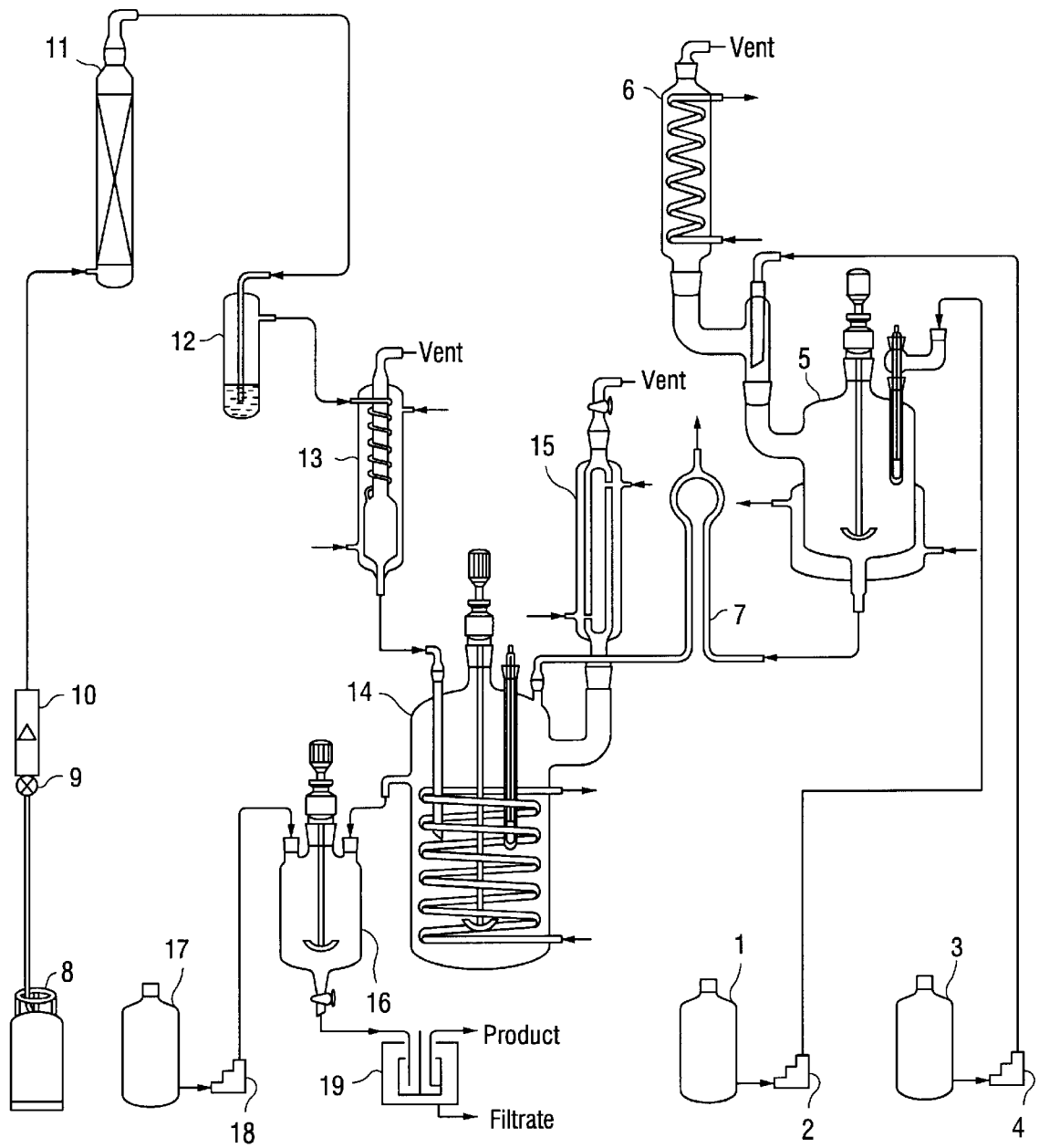

The present invention relates to a process for the preparation of 2-acrylamido-2-methyl-1-propanesulfonic acid. More particularly the said process is related to the preparation of highly pure 2-acrylamido-2-methyl-1-propanesulfonic acid in high yield, with improved appearance, by the reaction of acrylonitrile with more than 98% sulfuric acid or oleum and liquefied isobutylene in presence of weak inorganic acids or organic sulfonic acids.

BACKGROUND OF THE INVENTION 2-acrylamido-2methyl-1-propane-sulfonic acids as well as its homologues are used for improving the affinity of the acrylic fibers, towards dyes, in the dying process. 2-acrylamido-2-methyl-1-propane-sulfonic acid and its homologues function as co-monomers during the polymerization process with acrylic monomers. Further, the homopolymers or the copolymers of 2-acrylamido-2-methyl-1-propane sulfonic acid as well as its homologues, are used as extremely superior high molecular electrolytes and dispersants, thickeners, power failure prevention agents (2$^{nd}$ Gazette of American Patents No. 298371, Gazette 3332904 of the same patent). Apart from this, 2-acrylamido-2-methyl-1-propane-sulfonic acid as well as its congeners are also used as polymers with water absorption properties.

The manufacturing method for 2-acrylamido-2-methyl-1-propane-sulfonic acid as is known from the prior art, in general, comprises two steps. In step 1, acrylonitrile is reacted with concentrated sulfuric acid or oleum in presence of an additive at low temperatures. The resultant mixture is treated with isobutylene gas in the second step. Various methods of manufacturing 2-acrylamido-2-methyl-1-propane-sulfonic acid based on above general method have been suggested in the prior art.

Japanese Patent No JP 4074159 discloses the manufacture of 2-acrylamido-2-methyl-1-propanesulfonic acid by treating isobutylene gas with acrylonitrile and more than 95% conc. $H_2SO_4$ in the presence of organic carboxylic acids or their anhydrides. A mixture of 375 g acrylonitrile, and AcOH was treated drop wise with 98 g 100% $H_2SO_4$ at less than 0° C., introduced with 56 g of isobutylene gas at 30° C. over 52 min, then settled at room temperature for 1 h to give 186 g of 2-acrylamido-2-methyl-1-propane-sulfonic acid of 98.9% purity with APHA 20.

This method, while suitable for industrial production, referring to the examples cited in the above mentioned prior art, the yield is higher at 91.3% of theoretical on isobutylene, with corresponding purity of final product 2-acrylamido-2-methyl-1-propansulfonic acid is only 99.3%. Similarly, although the molar ratio of acrylonitrile to sulfuric acid is claimed to be greater than or equal to 4, all the examples use the acrylonitrile in the proportion of excess of 8.3 moles per mole of sulfuric acid. Such use of excess of acrylonitrile in the process leads to higher capital investment on recovery as well as higher operating cost of recovery at the industrial scale of manufacture. Furthermore, this method requires the reaction to be carried out at below 0° C. Therefore the cooling medium has to be provided at below sub-zero temperature resulting in increase in the cost of the utilities. Similarly, the total time required in this method for step 1 is 52 minutes while that for the step 2 is 1 hour. Thus, the reaction has to be carried out for a long time exceeding the total time by more than 112 minutes for both steps.

The use of organic carboxylic acids during the synthesis of 2-acrylamido-2-methyl-1-propane-sulfonic acid also leads to the formation of a thick slurry of the reaction mixture which poses difficulties in stirring as well as filtration. The quality of 2-acrylamido-2-methyl-1-propanesulfonic acid obtained in terms of purity and color specifications is also not satisfactory for the applications as mentioned above.

Japanese Patent No. JP 03077859 A2, discloses a method for manufacture of 2-acrylamido-2-methyl-1-propane-sulfonic acid from acrylonitrile, concentrated or fuming $H_2SO_4$ and isobutylene in the presence of various stabilizers A) Formula I

Formula I where $R_1$, $R_2$ are the same or different and are selected from hydrogen, amino, alkyl and alkylaryl or phenyl, lower alkyl having amino group as a substitute group or salts thereof. or B) Formula II Formula II:

where $R_1$ and $R_2$ are same as above; $R_1$ and $R_2$ can be $-CH_2$, $CH_2-NH-$, $R_3$ is selected from hydrogen, lower alkyl group, OH or $-N=C$ (Me); Y=O, S; or salts thereof or C) and adding inorganic reducing agents and, if necessary, solubilizers.

Although this method is also good for industrial production, the drawbacks are that, the isobutylene has to be used in gaseous form. In a continuous process, for handing gaseous isobutylene, the reactor has to be made of a specialized configuration to minimize the escape of unreacted isobutylene gas. This calls for a special arrangement which increases the capital cost of the hardware. Furthermore, the introduction of compounds represented by Formula I an Formula II as stabilizers, and the inorganic salts as solubilizers cause increase in the raw material cost and the processing costs leading also to contamination of the final product.

German Patent No. Ger. Offen. DE 290465 discloses a method for the manufacture of highly pure 2-acrylamido-2-methyl-1-propanesulfonic acid. High purity 2-acrylamido-2-methyl propanesulfonic acid (I), useful in the manufacture of dyeable acrylic polymers and of polyelctrolytes, is obtained by adding AcOH to crystalline I—containing slurry prepared from acrylonitrile, isobutylene, and concentrated or fuming $H_2SO_4$ or anhydrous sulfuric acid in a reaction medium, distilling to replace the reaction medium with AcOH, adding water or aq. $H_2SO_4$, heating to dissolve the sulfonic acid of formula I, and crystallizing it from the solution.

Although this method is simpler it involves additional steps of replacing the reaction medium with AcOH, heating and dissolution and recrystallization of product from the solution. These steps increase the cost of the process and the investment on industrial scale. In addition the yield loss due to the additional refining stages makes the process more uneconomical.

Japanese Patent No. JP 56103145 A2 discloses a method for manufacture of vinlyamides. Vinylamides of the formula $H_2C$: $CRCONHCMeR_1R_2$ I (R, $R_1$, $R_2$=H, Me, $CH_2SO_3Na$;

H, H, $C_6H_4SO_3Na^{-4}$; H, Me $CH_2OC_6H_4SO_3Na^{-4}$;H, H, $CH_2OC_6H_4SO_3Na^{-4}$; Me, Me, $CH_2SO_3Na$; H, Me, $CH_2SO_3H$; H, Me, $CH_2CI$) were prepared. Thus, 202 g>97% $H_2SO_4$ in AcOh was added to a mixture of $H_3C{:}CmeCH_2SO_3Na$ 158, H20 27, $H_2C{:}CHCN$ 106 g at >20 over 10 h to give, after 38 h, 195 g I (R=H, $R_1$=Me, $R_2$).

It is evident from this information that this method requires very long time of reaction, in excess of 48 hours. Therefore this method does not give any economical advantage on industrial scale.

Japanese Patent No. JP 02096559 A2 9, discloses a method for preparation of amidoalkanesulfonic acids as dispersants for calcium soaps as $R_1CONHCR_2R_3CR_4R_5SO_3H$ [$R_1$=hydrocarbyl; $R_2$ to $R_5$=H, (substituted) hydrocarbyl], useful as dispersants for Ca soaps, etc. (no data), or their precursors are prepared by treating nitriles and olefins with $SO_3$, $H_2SO_4$, or oleum and optionally with $H_2O$ in presence of 1 wt. % (per nitriles) carboxamides. Thus, a 573.0:12.6 (wt. ratio) mixture of $CH_2{:}CHCN$ and $CH_2{:}CHCONH_2$ was treated dropwise with oleum at 0–5° C. and stirred with $Me_2C{:}CH_2$ (I) at 50° C. for 1 h, and $H_2O$ was added to the reaction mixture to give 79.7% (based on I), $CH_2{:}CHCONHCMe_2CH_2SO_3H$ of 98.2% purity and APHA 5 (25% aq. Solution).

This method has the evident drawbacks of low purity and as well as low yields. Hence the product obtained by this method is not likely to be sufficient in quality for the applications mentioned above. And the process may not be economical on industrial scale due to poor yields.

OBJECTS OF THE INVENTION

The main object of the present invention is to provide a process for preparation of 2-acrylamido-2-methyl-1-propanesulfonic acid.

Another object of the present invention is to reduce the proportion of acrylonitrile compared to that of sulfuric acid in the reaction.

Still another object of the present invention is to avoid any additional raw material in the form of a stabilizer or solubilizer in the process.

Yet another object of the present invention is to carry out the process at temperatures greater the 0° C.

A further another object of the present invention is to reduce the total residence time of the reaction as low as possible.

Another object of the present invention is to provide a process for manufacture of 2-acrylamido-2-methyl-1-propane-sulfonic acid which obviates the difficulties in stirring and filtration during processing of 2-acrylamido-2methyl-1-propane-sulfonic acid.

SUMMARY OF THE INVENTION

Accordingly the present invention provides a process for preparation of 2-acrylamido-2-methyl-1-propane-sulfonic acid, which comprises mixing acrylonitrile with a mixture of sulfuric acid and a catalyst maintaining a maximum temperature of 20° C., followed by addition of isobutylene maintaining a maximum temperature of 50° C. and separating the product formed, purifying the product by washing with acrylonitrile followed by drying under vacuum at temperature 50 to 60° C.

In one embodiment of the invention strength of sulfuric acid is not less than 98%.

In another embodiment the catalyst is a weak inorganic acid such as othophosphoric acid, or an organic sulfonic acid selected from paratoluene sulfonic acid and benzene sulfonic acid, preferably partatoluene sulfonic acid.

In still another embodiment the ratio of acrylonitrile to mixture of sulfuric acid and catalyst is in the range of 3:1 to 6:1.

In yet another embodiment the ratio of catalyst to acrylonitrile is in the range of 0.02 to 100 to 4.0 to 100, preferably 0.3 to 1.

In still another embodiment the residual time for the retention of acrylonitrile with mixture of sulfuric acid and catalyst is in the range of 10 to 15 minutes, preferably 15 minutes.

In yet another embodiment isobutylene is added within a period of 10 to 15 minutes preferable 15 minutes.

BRIEF DESCRIPTION OF THE ACCOMPANYING DRAWING

In the drawing accompanying this specification, FIG. 1 represents the schematic of the experimental set-up for the process of manufacture of 2-acrylamido-2-methyl-1-propane-sulfonic acid showing one embodiment of the present invention.

DETAILED DESCRIPTION OF THE PRESENT INVENTION

The invention will now be explained with reference to the accompanying drawing. Using the device shown in FIG. 1 the continuation method of this invention was performed as follows: Acrylonitrile from 1 was continuously pumped into 5 at 500 g/h feed rate. 100% fuming $H_2SO_4$ pre-mixed with 4.5 wt % of 85% orthophosphoric acid from 2 was pumped into 5 at 131 g/h. 500 g of acrylonitrile was charged into 14 for start-up of stirrer before the overflow of 5 started collecting into 14. Isobutylene from 8 was liquefied in 13 and continuously fed to 14 at a rate of 60 g/h. The temperature in 5 was maintained at 12° C. The temperature in 14 was maintained at 40° C. The overflow of 14 was continuously collected into 16 for 3 hours so as to ensure complete steady state. After three hours, 2073 g of product slurry was collected in 16. The weight of hold-up material sucked out from main reactor 14 was 500 g. thus total product collected was 2573 g. This was filtered and the product dried in conventional dryer under reduced pressure. The weight of the final product, 2-acrylamido-2-methyl-1-propane-sulfonic acid, obtained was 603 g. [89.73% yield on isobutylene]. The purity of 2-acrylamido-2-methyl-1-propane-sulfonic acid obtained was 99.7%. The color on APHA scale was 15.

The following examples are given by way of illustration and should not be construed to limit the scope of present invention.

EXAMPLE-1

A glass reactor with a capacity of 1200 ml, was charged with 477 g of acrylonitrile containing 1900 ppm of water. Acrylonitrile to sulfuric acid molar ratio was 5.7. The glass reactor was provided with stirrer, funnel, vent condenser and thermometer. 85 wt % phosphoric acid 5 g was dissolved separately in 155 g of 100 wt % sulfuric acid in a dropping funnel. This mixture was charged to the acrylonitrile earlier stocked in 1200 ml capacity glass reactor within 20 minutes through dropping funnel while maintaining temperature at 10° C. 93.9 g of isobutylene gas was separately condensed in a dropping funnel type condenser. This liquefied isobutylene was added to the above reaction mixture as fast as possible maintaining the temperature at 30° C. The temperature was then allowed to rise slowly to 45° C. The 2-acrylamido-2-methyl-1-propane-sulfonic acid crystals were observed. The reaction mixture was slightly yellow in color. Very small amount of water was added to this reaction mixture and the yellow coloration vanished and very fine, and very white crystals could be seen in the slurry of the reaction mixture. This slurry of the product was sucked out from the reactor through a dip-tube. Formed crystals were filtered and washed with 200 g of acrylonitrile. The product 2-acrylamido-2-methyl-1-propane-sulfonic acid crystals were dried under reduced pressure at 60° C., to give 298 g of dry product. [89.6% of theoretical yield on isobutylene]. The purity of 2-acrylamido-2-methyl-1-propanesulfonic acid crystals was 99.5% and the color on APHA scale was 15.

EXAMPLE-2

The experimental procedure followed was similar to that of Example 1, except the quantity of acrylonitrile used was 716 g, containing 1940 ppm water. Acrylonitrile to sulfuric acid molar ratio was 7.65, the quantity of 100% sulfuric acid was 173 g. The quantity of isobutylene used was 99 g. The quantity of acrylonitrile used for wash was 250 g. The quantity of final product obtained was 315 g. representing 86% of the theoretical yield on isobutylene. The product was very white in color. Purity by acidity was 99.48%, while that by unsaturation was 98.9%. The color on APHA scale was 15.

EXAMPLE-3

The experimental procedure followed was very similar to that of Example 1, except the quantity of acrylonitrile used was 434 g, containing 1013 ppm water. Acrylonitrile to sulfuric acid molar ratio was 7.64, the quantity of 100% sulfuric acid was 105 g. The quantity of isobutylene used was 60 g. The quantity of acrylonitrile used for wash was 219 g. The quantity of final product obtained was 197 g, representing. 88.8% of theoretical yield on isobutylene. The purity by unsaturation was 99.7% and that by acidity was 101.26%. The color on APHA scale was 15.

EXAMPLE-4

The experimental procedure followed was very similar to that of Example 1, except the quantity of acrylonitrile used was 434 g, containing 1900 ppm water. Acrylonitrile to sulfuric acid molar ratio was 7.64. The quantity of 100% sulfuric acid was 105 g. The quantity of para toluene sulfonic acid dissolved in sulfuric acid was 5 g. The quantity of para toluene sulfonic acid dissolved in sulfuric acid was 5 g. The quantity of isobutylene used was 60 g. The quantity of acrylonitrile used for was 200 g. The quantity of final product obtained was 190 g, representing 85.7% of theoretical yield on isobutylene. Derived 2-acrylamido-2-methyl-1-propane-sulfonic acid was slightly off-white; its purity was 99.5%. The color on APHA scale was 20.

EXAMPLE-5

The experimental procedure followed was very similar to that of Example 4, except the acrylonitrile used contained 6823 ppm water [acrylonitrile to sulfuric acid molar ratio was 7.64]. The para toluene sulfonic acid was dissolved in acrylonitrile. instead of sulfuric acid. The quantity of acrylonitrile used for wash was 240 g. The quantity of final product obtained was 182 g. representing 85.7% of theoretical yield on isobutylene. Derived 2-acrylamido-2-methyl-1-propanesulfonic acid was white in color. Its purity by unsaturation was 98.9% while the purity by acidity was 99.87%. The color on APHA scale was 15.

EXAMPLE-6

Using the device shown in FIG. I the continuation method of this invention was performed as follows: Acrylonitrile from 1 was, continuously pumped into 5 at 500 g/h feed rate. 100% fuming $H_2SO_4$ pre-mixed with 4.5 wt % of 85% orthophosphoric acid from 2 was pumped into 5 at 131 g/h. 500 g of acrylonitrile was charged into 14 for start-up of stirrer before the overflow of 5 started collecting into 14. Isobutylene from 8 was liquefied in 13 and continuously fed to 14 at a rate of 60 g/h. The temperature in 5 was maintained at 12° C. The temperature in 14 was maintained at 40° C. The overflow of 14 was continuously collected into 16 for 3 hours so as to ensure complete steady state. After three hours, 2073 g of product slurry was collected in 16. The weight of hold-up material sucked out from main reactor 14 was 500 g. thus total product collected was 2573 g. This was filtered and the product was dried in conventional dryer under reduced pressure. The weight of the final product, 2-acrylamido-2-methyl-1-propane-sulfonic acid, obtained was 603 g. [89.73% yield on isobutylene]. The purity of 2-acrylamido-2-methyl-1-propane-sulfonic acid obtained was 99.7%. The color on APHA scale was 15.

The Main Advantages of the Present Invention Are:

1. This method permits the reaction of the acrylonitrile and concentrated or fuming sulfuric acid to be carried out at comparatively higher degree temperature.
2. The molar ratio of acrylonitrile to sulfuric acid is reduced compared to the other methods of the past. Thus the cost of recovery and recycle of unreacted acrylonitrile is reduced.
3. The method of this invention does not require any additional stabilizer or solubilizer thus reducing raw material cost and avoiding chances of contamination
4. The method covered by this invention reduces the total reaction time by at least 50% compared to that of 112 minutes reported as best in the past methods. Thus the capital cost per unit weight of production of 2-acrylamido-2-methyl-1-propane-sulfonic acid is reduced if the methods of this invention are followed for industrial manufacture of 2-acrylamido-2methyl-1-propane-sulfonic acid
5. 2-acrylamido-2-methyl-1-propane-sulfonic acid obtained by the methods of this invention, does not appear yellow like usual products but has brilliant white color, and even if there is coloration, compared with usual products it appears at the most off white, but essentially it being white, the purity is raised almost above 99% and it is not necessary to manufacture specially for normal usage
6. The product 2-acrylamido-2-methyl-1-propane-sulfonic acid manufactured by the methods of present invention is essentially in the form of very fine granules having very good filtration and drying characteristics. Therefore the difficulties in stirring, filtration and drying are minimized compared to the other method of the past.
7. Moreover the yield on limiting reactant isobutylene in this method is also high.

Thus in the methods of this invention, as compared to the usual methods, extremely high quality goods are obtained in high yields at relatively lower cost of production and stable 2-acrylamido-2-methyl-1-propane-sulfonic acid of very high purity can also be produced.

We claim:

1. A process for the preparation of 2-acrylamido-2-methyl-1-propane-sulfonic acid, which comprises mixing acrylonitrile with a mixture of sulfuric acid and a catalyst while maintaining a maximum temperature of 20° C., the ratio of acrylonitrile to mixture of sulfuric acid and catalyst being in the range of 3:1 to 6:1 and the ratio of catalyst to acrylonitrile being in the range of 0.02 to 100 to 4.0 to 100, followed by addition of isobutylene while maintaining a maximum temperature of 50° C. and separating the product formed, purifying the product by washing with acrylonitrile followed by drying under vacuum at a temperature in the range of 50 to 60° C. to obtain the desired product.

2. A process as claimed in claim 1 wherein the strength of sulfuric acid is not less than 98%.

3. A process as claimed in claim 1 wherein the catalyst is a weak inorganic acid selected from othophosphoric acid and polyphosphoric acid.

4. A process as claimed in claim 1 wherein the catalyst is phosphorus pentoxide.

5. A process as claimed in claim 3 wherein the catalyst is orthophosphoric acid.

6. A process as claimed in claim 1 wherein the catalyst is an organic sulfonic acid selected from paratoluene sulfonic acid and benzene sulfonic acid.

7. A process as claimed in claim 6 wherein the catalyst is paratoluene sulfonic acid.

8. A process as claimed in claim 1 wherein the ratio of catalyst to acrylonitrile is 0.3 to 1.

9. A process as claimed in claim 1 wherein the residual time for the retention of acrylonitrile with mixture of sulfuric acid and catalyst is in the range of 10 to 20 minutes.

10. A process as claimed in claim 1 wherein the residual time for the retention of acrylonitrile with mixture of sulfuric acid and catalyst is 15 minutes.

11. A process as claimed in claim 1 wherein the addition of isobutylene is made within a period of 10 to 20 minutes.

12. A process as claimed in claim 1 wherein the addition of isobutylene is made in a period of 15 minutes.

* * * * *